United States Patent [19]

Reesink et al.

[11] 4,351,935

[45] Sep. 28, 1982

[54] THERMOSETTING COATING COMPOSITION CONTAINING A BLOCKED ACID CATALYST

[75] Inventors: Johan B. Reesink, Didam; Hendrik J. Hageman, Rozendaal; Ulfert E. Wiersum, Velp, all of Netherlands

[73] Assignee: Akzo N.V., Arnhem, Netherlands

[21] Appl. No.: 283,332

[22] Filed: Jul. 14, 1981

[30] Foreign Application Priority Data

Jul. 14, 1980 [NL] Netherlands .......................... 8004031

[51] Int. Cl.$^3$ ...................... C08G 12/12; C08G 12/32; C08L 61/32

[52] U.S. Cl. ..................................... 528/242; 427/27; 428/460; 524/33; 524/35; 525/160; 525/162; 525/443; 528/254; 528/258; 528/259

[58] Field of Search ............... 528/242, 487, 254, 258; 525/157, 509

[56] References Cited

U.S. PATENT DOCUMENTS

4,038,226 7/1977 Towle et al. ........................ 260/22

4,083,830 4/1978 Gallagher .......................... 525/509

FOREIGN PATENT DOCUMENTS

2731528 1/1978 Fed. Rep. of Germany .
2125962 9/1972 France .

OTHER PUBLICATIONS

Titov et al.; Chem. Abstract, vol. 70, 1969, p. 40 (88677e).

*Primary Examiner*—Theodore E. Pertilla
*Attorney, Agent, or Firm*—Stevens, Davis, Miller & Mosher

[57] ABSTRACT

A thermosetting coating composition contains an acid-curable amino resin and from 0.1 to 10 percent by weight of a blocked sulphonic acid calculated on the weight of amino resin. In order to reduce the electric conductivity of the composition after a prolonged pot-life, a sulphonic acid oximate is used as the blocked acid.

The compositions are advantageous for coating a substrate by electrostatic spraying.

10 Claims, No Drawings

THERMOSETTING COATING COMPOSITION CONTAINING A BLOCKED ACID CATALYST

This invention relates to a thermosetting coating composition containing an acid-curable amino resin and such an amount of a blocked acid as corresponds to 0.1 to 10 percent by weight, calculated on the amino resin of potentially available suphonic acid.

A thermosetting coating composition of the type indicated above is described in German Pat. Spec. No. 2,731,528. The blocked acids disclosed in the German specification are obtained from a sulphonic acid and epoxidized compounds (oxiranes), encompassing both the low-molecular weight epoxides such as ethylene oxide, propylene oxide and the like and epoxy resins.

A disadvantage to the blocked acids disclosed in the German specification is that the conductivity of coating compositions containing these compounds will increase rapidly to a value which may give problems when these compositions are to be applied to a substrate by electrostatic spraying.

It is therefore an object of this invention to provide a thermosetting coating composition containing an acid-curable amino resin which is devoid of the aforesaid disadvantage and is adapted for application on a substrate by electrostatic spraying. Another object of the invention is to provide an improved coating composition containing an acid curable amino resin and a blocked acid. Still another object of the invention is to provide articles having an improved coating of a thermosetting amino resin.

The foregoing objects and others are accomplished in accordance with this invention, generally speaking, by providing a thermosetting coating composition containing an acid curable amino resin and blocked acid that is less likely to cause problems because of low electrical resistance. The thermosetting coating composition contains as a blocked acid a compound which corresponds to any one of the following formulae:

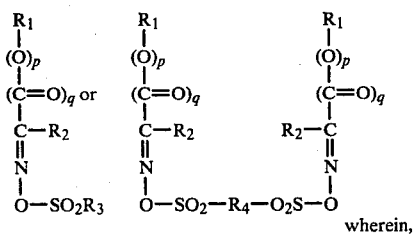

wherein, wherein, p=O or 1 and q=O or 1, and $R_1$ is a substituted or unsubstituted alkyl group, alkenyl group, cycloalkyl group, cycloalkenyl group, aryl group, aralkyl group, aralkenyl group or heterocyclic group having not more than 20 carbon atoms; $R_2$ has the same meansing as $R_1$ or is an $NH_2$, CN, a substituted or unsubstituted alkoxy carbonyl group, cycloalkoxy carbonyl group, aroxy carbonyl group or acyl group having not more than 20 carbon atoms, or the two groups $R_1$ and $R_2$ form part of a cyclic or heterocyclic group having not more than 12 atoms in the ring; $R_3$ is a substituted or unsubstituted alkyl group, alkenyl group, cycloalkyl group, cycloalkenyl group, aryl group or heterocyclic group having not more than 30 carbon atoms and $R_4$ represents a substituted or unsubstituted alkylene group, alkenylene group, cycloalkylene group, cycloalkenylene group, arylene group or bifunctional heterocyclic group having not more than 35 carbon atoms. Examples of suitable substituents in the groups $R_1$, $R_2$, $R_3$ and $R_4$ of the above structural formula include the halogens fluorine, bromine or iodine; nitro groups, cyano groups and alkoxy or alkanoyl groups. Optionally, one or more ethylenically unsaturated groups may be present. This may be of particular importance if besides curing under the influence of an acid there will be further curing under the influence of radical reactions. It has been found that within the scope of the invention generally satisfactory results are obtained with coating compositions containing a blocked acid of any one of the above formulae wherein when p=O and q=1, $R_1$ and $R_2$ represent an aryl group and when p=1 and q=1, $R_1$ represents an alkyl group or a cycloalkyl group and $R_2$ represents an alkyl group, a cycloalkyl group or an aryl group.

Partly because of the availability of the starting materials and the method of preparing the present compositions preference is given to compounds of any one of the above formulae, wherein p=O and q=1, $R_1$ and $R_2$ represent a phenyl group, and when p=1 and q=1, $R_1$ represents a lower alkyl group and $R_2$ a lower alkyl group or phenyl group. Coating compositions of improved storage stability are also obtained when one or more of the following compounds

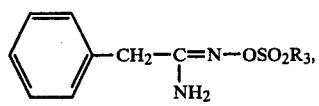

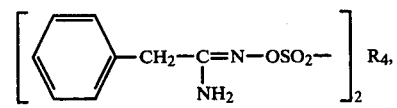

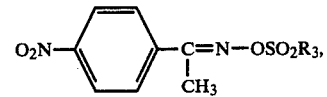

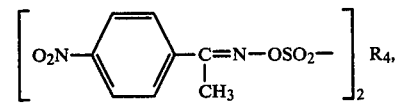

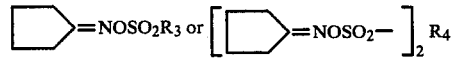

is used.

Very favorable results are generally obtained when $R_3$ represents a p-tolyl group or an alkyl group having 1 to 18 carbon atoms.

Coatings possessing extraordinarily good properties are obtained when $R_4$ is a dialkyl naphthalene group having not more than 35 carbon atoms. Most preferred compounds are those in which $R_4$ is a dinonyl or a didodecyl naphthalene group. It is preferred that these nonyl groups or dodecyl groups should be highly branched.

Examples of suitable blocked acids for the present coating compositions include:
benzil monoxime tosylate;
furil monoxime tosylate;

acetone oxime cetyl sulphonic acid ester;
cyclopentanone oxime oleyl sulphonic acid ester;
p-nitro acetophenone oxime tosylate;
2-hydroximinopropiophenone tosylate;
α-oximinophenyl acetic acid ethyl ester tosylate;
α-oximinocaproic acid ethyl ester tosylate;
benzyl amido oxime tosylate;
cyclopentanone oxime butyl sulphonic acid ester;
cyclohexanone oximethyl sulphonic acid ester;
p-chloro acetophenone oxime octyl sulphonic acid ester;
di(2-naphthyl)-diketone monoxime ethyl sulphonic acid ester;
propiophenone oxime tosylate;
1-(2-furyl)-1-butanone oxime tosylate;
the dinonyl naphthalene disulphonic acid diester of benzil monoxime α-oximinobenzoyl acetic acid ethyl ester tosylate, and the like.

The blocked acids may be prepared by any known conventional process. In one attractive process, a monoketone or diketone is reacted with hydroxylamine or, preferably, with the hydrochloric acid salt thereof.

After conversion of the salt of the hydroxylamine into the oxime by treating it with an aqueous sodium hydroxide solution, the oxime is dissolved in an organic solvent such as tetrahydrofuran, followed by successively adding an amine and the acid chloride of a sulphonic acid. The resulting sulphonic acid ester of the oxime is subsequently isolated.

In another process an active methylene compound is first reacted with sodium alcoholate, followed by adding a solution of nitrite ester. After concentration by evaporation and further processing and extraction, the desired oxime is obtained. The oxime is reacted, in the presence of an amine, with the acid chloride of the required sulphonic acid. The resulting sulphonic acid ester of the oxime is subsequently isolated.

The blocked acid to be used in the coating composition according to the invention may be employed in any suitable amount, preferably in an amount of 0.1 to 10 percent by weight, calculated on the weight of the amino resin of potentially avaiable sulphonic acid. Generally, there is no need to use more than 0.3 to 2% by weight of the blocked acid, calculated on the solid constituents of the coating composition. Any suitable acid-curable amino resins may be used in the coating composition of the invention. The amino resins are as a rule obtained by condensation of an aldehyde such as formaldehyde and a urea, melamine or guanamine and the lower alkyl ethers thereof. A particularly atttractive group of amino resins is the methylated melamine formaldehyde resins, including hexamethyoxy-methyl melamine and the mixed peralkoxy derivatives thereof. This hexamethoxymethy melamine may, for instance, be reacted with an alkyd resin under conditions such that a minimum degree of cross-linking occurs. The actual cross-linking will not occur until the acid is unblocked and released when the blocked acid-containing composition is heated.

In addition to the acid-curable amino resin there may still be present another co-condensing polymer. Such a polymer should contain at least two hydroxyl, carboxyl, amine and/or amide groups.

The co-condensable polymers may be addition or condensation polymers. Examples of suitable addition polymers include the homopolymers and the copolymers of acrylic and methacrylic acid and other unsaturated monomers or mixtures of monomers; the homopolymers and the copolymers of ethylenically unsaturated monomers such as styrene, substituted styrene; vinyl esters such as vinyl acetate, vinyl propionate and the like; α-olefins such as ethylene, propylene, 1-butene, 1-octene; vinyl chloride, vinylidene chloride, conjugated dienes such as 1,3-butadiene; fluorine-containing olefins such as vinyl fluoride and hexafluoropropylene; vinyl ether and allyl ether; and the mono- and the diesters of α,β-ethylenically unsaturated dicarboxylic acids such as mono- and dialkyl maleates, mono- and dialkyl fumarates, mono- and dialkyl itaconates.

The functional groups that are needed for effecting a condensation reaction with the acid-curable amino resin may be introduced during the preparation of the polymer or afterwards.

Examples of suitable monomers include hydroxyethyl acrylate, hydroxypropyl acrylate, hydroxyethyl methacrylate, hydroxypropyl methacrylate, acrylic acid, methacrylic acid, itaconic acid, maleic acid, N-t-butyl-aminoethyl methacrylate, acrylamide and/or methacrylamide.

One example of a postcondensation reaction is the hydroxy methylation of an amide-containing polymer.

Examples of condensation polymers include the alkyd resins derived from a polyhydric alcohol and a polybasic acid. They include polyesters that may be modified or not with fatty acids and/or polyethers. The diols that are suitable for use in the preparation of the polyesters may be aliphatic or aromatic. Examples of suitable diols include ethylene glycol; propylene glycol-1,2; propylene glycol-1,3; butane diol-1,2; butane diol 1,3; butane diol-1,4; neopentyl glycol; 2,2,4-trimethylpentane-1,3-diol; decamethylene glycol; monoethyl ether of glycerol and/or the α-β allyl ether of glycerol. The dicarboxylic acids suitable for use in the preparation of the polyesters may be aliphatic, cycloaliphatic or aromatic.

Suitable dicarboxylic acids are malonic acid, succinic acid, glutaric acid, adipic acid, pimelic acid, suberic acid, azelaic acid, maleic acid, fumaric acid, tetrahydrophthalic acid, dilinoleic acid, diphenic acid, tetrachlorphthalic acid, isophthalic acid, terephthalic acid, o-phthalic acid, cyclohexane-1,2-dicarboxylic acid, the maphthalene dicarboxylic acids and/or trimethyl adipic acid.

Also suitable for use in the coating compositions are natural polymers based on cellulose or derivatives thereof such as regenerated cellulose. The following examples are submitted for a better understanding of the invention. They are, of course, not to be construed as being limiting in any manner whatsoever.

The test methods mentioned in the examples below were all carried out in accordance with ASTM and the DIN standards mentioned. The Persoz hardness was determined in conformity with the French NF-Standard T-30-016.

In the examples the following ester diols were employed, use being made in all cases of hexamethoxymethyl melamine as cross-linking agent.

Diester diol I: a mixture of equal parts by weight of (a) di(monodecanoic acid ester of trimethylol propane)-isophthalate and (b) a mixture of 1 part of di(neopentyl glycol)-isophthalate and 2 parts of di(neopentyl-glycol)phthalate.

Diester diol II: a 90% by weight solution in xylene of 1 part of di(neopentyl glycol)isophthalate, 1 part of di(neopentyl glycol)orthophthalate and 2 parts of dimer of di(3-methylpentane diol-1,5)isophthalate.

Diester diol III: an alkyd resin made up of 28% by weight of fatty acids, 47% by weight of phthalic anhydride and 25% by weight of polyalcohols.

EXAMPLE I

Preparation of β-benzil monoxime tosylate 210 g of benzil were suspended in 200 ml of ethanol and cooled to −5° C. To this suspension 70 g of hydroxylamine hydrochloride were gradually added in portions and at a rate such that the temperature of the reaction mixture did not exceed 0° C.

Subsequently, 120 g of NaOH in 600 ml of water were added with vigorous stirring at a temperature of −5° to −3° C., at which temperature stirring was continued for 1½ hours. The reaction mixture was diluted with 1 liter of cold water and the non-converted benzil was filtered off. The filtrate was acidified with acetic acid and a white product precipitated. This product was washed with water and air dried. The yield was 209 g of an α-benzil monoxime, which was subsequently converted into the β-isomer by dissolving it in 2 liters of benzene, to which 15 g of active carbon had been added, which suspension was boiled for 15 minutes with refluxing. After filtration of the carbon the filtrate was concentrated by evaporation under reduced pressure.

The yield of β-benzil monoxime was 152 g. Of this substance 67.5 g were dissolved in 150 ml of tetrahydrofuran and cooled to −5° C. Next, there were added 45.5 g of triethylamine and subsequently, over a period of 45 minutes and at a temperature of −5° to 0° C. with vigorous stirring, 57 g of p-toluene sulphonyl chloride in 150 ml of tetrahydrofuran. After 30 minutes stirring the mixture was poured into 1 liter of cold water and 40 ml of concentrated hydrochloric acid. The solid matter was filtered off, washed with cold water and dried over phosphorus pentoxide. Following recrystallization from a mixture of 3 parts of ethanol and 2 parts of acetone, 58.7 g of very pure benzil monoxime tosylate (melting point 113.3°–115.5° C.) were obtained.

EXAMPLE II

Preparation of p-nitroacetophenone oxime tosylate 42 g (=0.6 mole) of hydroxylamine hydrochloride were successively dissolved in 90 ml of water and cooled in ice. Subsequently, 18 g of NaOH (0.3 mole) in 50 ml of water were added with proper stirring and cooling. To the resulting solution there were added 49.5 g of p-nitro-acetophenone in 200 ml of ethanol followed by heating under reflux. Next, another 200 ml of ethanol were added, so that all solid matter went into solution. The solution was still boiled for 1 hour under reflux. After cooling in ice, a pale yellow product was obtained, which was filtered off, washed with water and dried.

The yield of p-nitroacetophenone oxime was 51 g.

In a following step 18 g of p-nitroacetophenone oxime in 300 ml of acetone were added to a solution cooled to 0° C. of 4 g of NaOH (0.1 mole) in 50 ml of water. Next, 19.4 g (0.102 mole) of p-toluene sulphonyl chloride in 100 ml of acetone were added, with stirring and at a temperature of 5° to 10° C.

After the solution had successively been stirred for 1 hour at 0° to 5° C. and poured into 300 ml of benzene, it was washed four times with 125 ml of cold water and dried.

After the benzene had been distilled off, a yellow residue remained, which after recrystallization from a mixture of benzene and hexane (1:1) had a melting point in the range of 123.4° to 125.4° C.

EXAMPLE III

Preparation of α-oximinocaproic acid ethyl ester tosylate 21.6 g (0.1 mole) of n-butyl-diethyl malonate were cooled to −10° C. followed by adding to it 15.6 g (0.133 moles of isoamyl nitrite. To this mixture a solution of 2.3 g of Na (0.1 mole) in 45 ml of ethanol (anhydrous) was added, with stirring, over a period of 1½ hours at a temperature between −10° and −8° C. Stirring was continued for 16 hours at −10° C. After evaporation and further treatment with cold water, extraction with ether, acidification and a second extraction with ether, 13.8 g of α-oximino-caproic acid ethyl ester were obtained.

5.3 g (0.03 mole) thereof were dissolved in 25 ml of tetrahydrofuran, cooled to −10° C., after which 4.55 g (0.045 mole) of triethylamine were added. To this solution there was added, over a period of 1 hour and at a temperature between −10° and 0° C., a solution of 5.7 g (0.03 mole) of p-toluene sulphonyl chloride in 25 ml of tetrahydrofuran. After 1 hour's stirring at 0° C., the reaction mixture was stored for 16 hours at 4° C. and subsequently poured into cold dilute hydrochloric acid and extracted three times with 100 ml of diethyl ether. After drying with magnesium sulphate, the ether was distilled off. The product was recrystallized from ethanol and had a melting point of 43.2° –46.8° C.

EXAMPLE IV

A pigment dispersion was prepared by mixing 24 parts of titanium white with 3 parts of an acrylate resin, 7.5 parts of hexamethoxymethyl melamine, 1 part of xylene and 1 part of ethylglycol acetate. To the resulting mixture there was added diester diol I in a ratio of 3 parts of diester diol to 1 part of hexamethoxymethyl melamine. The pigment-resin ratio was 0.67. Into this coating composition there was incorporated a 10%-solution in methylisobutyl ketone of syn-benziloxime tosylate in an amount which corresponds to 0.7% by weight of p-toluene sulphonic acid, calculated on the solid constituents. The paint composition was diluted with a mixture of xylene and ethylene glycol monoethyl ether acetate (1:1) until the viscosity obtained corresponded to an efflux time of 39 seconds in a G2 Zahn cup.

Part of the coating composition thus prepared was applied to a phosphated iron panel and cured for 25 minutes at 130° C. The properties of the resulting paint film and the change in viscosity of the composition during storage at 50° C. are summarized in Table I.

TABLE I

| | |
|---|---|
| thickness determined in accordance with ASTM D1186-53 | 40–45 mm |
| gloss 20° in accordance with ASTM D523 | 9.5% |
| Persoz hardness in accordance with NF T30-016 | 298 seconds |
| conical mandrel test in accordance with ASTM 522-60 (9 mm) | 12 |
| Ford falling weight test (kg cm) ASTM D2794-69 | |
| upper side | 45 |
| under side | 30 |
| Erichsen indentation test (mm) in conformity with DIN 53156 | 6.8 |
| change in viscosity with storage at 50° C. (G2 Zahn cup, sec) | |
| initial viscosity | 39.4 |

TABLE I-continued

| | |
|---|---|
| after 4 weeks | 77 |

Another part of the coating composition was used to establish the influence of the presence of a blocked acid on the electric conductivity of resistance as a function of time. To that end four coating compositions were prepared, one of which (the blank) contained no acid and the others a blocked or non-blocked acid in such an amount as was needed to obtain a coating having the same mechanical properties after 25 minutes curing at 130° C.

The resistance was measured immediately after preparation and again after storage times of 2 and 4 weeks at 35° C. The results are summarized in the table below. Composition No. 1 contained as catalyst a commercially available acid blocked with an epoxy compound, according to German Pat. Specification No. 2,731,528, under the chemical name 2,3-epoxypropyl-1,1-dimethyl heptane carboxylate.

Composition No. 2 contained syn benzyl monoxime tosylate according to the invention. Composition No. 3 contained no catalyst and Composition No. 4 contained non-blocked p-toluene sulphonic acid as catalyst. The catalyst concentrations given in the table are all in percent by weight p-toluene sulphonic acid, calculated on the solid constituents.

TABLE II

| Composition | Catalyst concentration | Resistance, k Ω | | |
|---|---|---|---|---|
| | | | after | |
| | | initially | 2 weeks | 4 weeks |
| 1 | 1 | 3000 | 500 | 500 |
| 2 | 0,7 | 3750 | 1650 | 1250 |
| 3(1) | — | 5500 | 6000 | 6000 |
| 4 | 0,5 | 290 | 350 | 400 |

(1)after curing for 25 minutes at 130° C. the mechanical properties were deficient.

The above results clearly show the great advantage obtained by the use of the catalyst of the present invention (in Composition No. 2). The amount in which it need to be added may be considerably smaller than that of the known catalyst in Composition No. 1, its electric resistance not only being satisfactory at the start, but even after storage times of 2 and 4 weeks, which cannot be said of the resistance of Composition No. 1.

EXAMPLE V 2 parts of diester diol II were mixed with 1 part of hexamethoxymethyl melamine and such an amount of oxime blocked sulphonic acid as corresponds to 0,6% by weight of p-toluene sulphonic acid (calculated on the solid constituents). The resulting composition was subsequently diluted with a mixture of equal parts by weight of xylene and ethylene glycol monoethyl ether acetate until it was brought to spraying consistency.

The paint was applied to a phosphated iron panel and cured for 30 minutes at 130° C. The thickness of the coating applied was determined in accordance with ASTM D1186-53 and the Persoz hardness in accordance with NF T30-016. Also determined were both the initial viscosity and the viscosity after 4 weeks' storage at 40° C. The viscosity was determined by meansuring the efflux time (in seconds) in a Ford cup No. 4. The results are given in Table III below.

TABLE III

| blocked acid | paint properties | | viscosity (Ford cup No. 4) | |
|---|---|---|---|---|
| | thickness (μ) | Persoz hardness | initial | after 4 weeks at 40° C. (sec) |
| p-nitro acetophenone oxime tosylate | 25 | 367 | 35 | 56 |
| syn benzil monoxime tosylate | 25 | 365 | 31 | 71 |
| α-oximinocaproic acid ethyl ester tosylate | 25 | 363 | 33 | 62 |
| α-oximinophenyl acetic acid ethyl ester tosylate | 25 | 340 | 33 | 70 |
| benzylamidoxime tosylate | 25–30 | 336 | 31 | 90 |
| syn benzil monoxime mesylate | 23 | 368 | 31 | 60 |
| syn benzil monoxime cetyl sulphonic acid ester | 28 | 332 | 34 | 40 |

EXAMPLE VI 31.1 g of diester diol III were mixed with 5.5 g of hexamethoxymethylmelamine and 0.44 g of benzil oxime tosylate.

The resulting paint was subsequently diluted with xylene until it was at spraying consistency. The paint was applied to a phosphated iron panel and cured for 30 minutes at 130° C.

Repeating the procedure described hereinbefore, the thickness of the paint coating, the Persoz hardness and the storage stability at 40° C. (change in viscosity in a Ford cup No. 4 over a period of 4 weeks) were determined. The results are given below:

| | |
|---|---|
| thickness of paint coating | 25μ |
| Persoz hardness (sec) | 327 |
| the viscosity rose from 20 to 60 seconds. | |

Although the invention has been described in detail for the purpose of illustration, it is to be understood that such detail is solely for that purpose and that variations can be made therein by those skilled in the art without departing from the spirit and scope of the invention except as it is limited by the claims.

What is claimed is:

1. A thermosetting coating composition containing an acid-curable amino resin and an amount of a blocked acid corresponding to 0.1 to 10 percent by weight, calculated on the amino resin of potentially available sulphonic acid, said blocked acid having one of the following formulae:

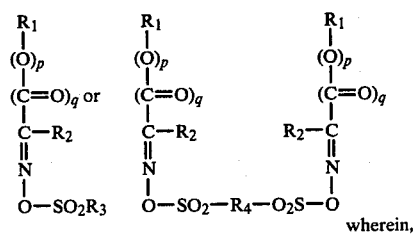

wherein, p=0 or 1 and q=0 or 1, and $R_1$ is a substituted or unsubstituted alkyl group, alkenyl group, cycloalkyl group, cycloalkenyl group, aryl group, aralkyl group, aralkenyl group or heterocyclic group having not more than 20 carbon atoms;

$R_2$ is the same as $R_1$, $NH_2$, CN, an alkoxy carbonyl group, cycloalkoxy carbonyl group, aroxy carbonyl group or acyl group having not more than 20 carbon atoms, or the two groups $R_1$ and $R_2$ form part of a cyclic or heterocyclic group having not more than 12 atoms in the ring;

$R_3$ is an alkyl group, alkenyl group, cycloalkyl group, cycloalkenyl group, aryl group or heterocyclic group having not more than 30 carbon atoms and $R_4$ is an alkylene group, alkenylene group, cycloalkylene group, cycloalkenylene group, arylene group or bifunctional heterocyclic group having not more than 35 carbon atoms.

2. The coating composition of claim 1, wherein $p=0$ and $q=1$, $R_1$ and $R_2$ are aryl groups and, when $p=1$ and $q=1$, $R_1$ is an alkyl group or a cycloalkyl group and $R_2$ is an alkyl group, a cycloalkyl group or an aryl group.

3. The coating composition of claim 2, wherein $p=0$ and $q=1$, $R_1$ and $R_2$ are phenyl groups, and when $p=1$ and $q=1$, $R_1$ is a lower alkyl group and $R_2$ is a lower alkyl group or phenyl group.

4. The coating composition of claim 1, wherein the blocked acid is a compound of the formula

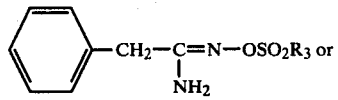

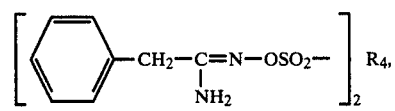

5. The coating composition of claim 1, wherein the blocked acid is a compound of the formula

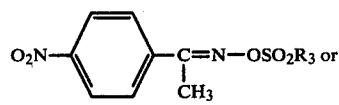

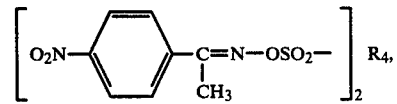

6. The coating compositon of claim 1, wherein the blocked acid is a compound of the formula

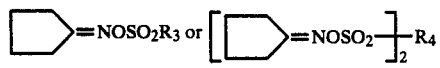

7. The coating composition of claim 1, 2, 3, 4, 5 or 6, wherein $R_3$ is a p-tolyl group or an alkyl group having 1 to 18 carbon atoms.

8. The coating composition of claim 1, 2, 3, 4, 5 or 6, wherein $R_4$ is a dialkyl naphthalene group having not more than 35 carbon atoms.

9. The coating composition of claim 8, wherein the dialkyl naphthalene group is a dinonyl or a didodecyl naphthalene group.

10. As a new article of manufacture, an article coated with the coating composition of claim 1.

* * * * *